United States Patent [19]

Makovec et al.

[11] 4,205,196

[45] May 27, 1980

[54] ACID-TYPE HYDROCARBON ALKYLATION WITH ACID RECYCLE STREAMS AT SPACED POINTS OF A VERTICALLY-DISPOSED ELONGATED REACTOR

[75] Inventors: Donald J. Makovec; Donald M. Haskell, both of Bartlesville, Okla.

[73] Assignee: Phillips Petroleum Company, Bartlesville, Okla.

[21] Appl. No.: 27,426

[22] Filed: Apr. 5, 1979

[51] Int. Cl.$^2$ .................. C07C 3/54; G01N 25/00; B01J 8/00

[52] U.S. Cl. .................. 585/701; 585/716; 585/723; 585/727; 585/730; 585/401; 585/911; 585/926; 422/111; 422/234; 422/235; 23/230 A

[58] Field of Search ............ 585/375, 447, 701, 716, 585/401, 723, 727, 730; 422/111, 234, 235; 23/230 A

[56] References Cited

U.S. PATENT DOCUMENTS

| 3,080,438 | 3/1963 | Sailors | 585/723 |
| 3,169,152 | 2/1965 | Van Pool et al. | 585/701 |
| 3,169,153 | 2/1965 | Walker et al. | 585/714 |
| 3,249,649 | 5/1966 | Sherk et al. | 585/714 |
| 3,998,903 | 12/1976 | Sobel | 585/723 |

*Primary Examiner*—George Crasanakis

[57] ABSTRACT

A method of alkylating an alkylatable hydrocarbon with different alkylating agents, at different reaction temperatures and in a single reaction zone, in which an alkylatable hydrocarbon is contacted with an acid-type catalyst and at different points in an elongated reaction zone, the reaction zone effluent is separated into a hydrocarbon phase and a catalyst recycle phase and the reaction temperatures of the various alkylating agents are maintained at different temperatures by splitting the recycle catalyst phase into an equal number of streams and adjusting the reaction temperatures by adjusting the temperatures of the recycle catalyst phase streams, the relative proportions of the recycle catalyst phase streams or both. A method of starting-up the process and apparatus for conducting the process are also disclosed.

36 Claims, 3 Drawing Figures

ACID-TYPE HYDROCARBON ALKYLATION WITH ACID RECYCLE STREAMS AT SPACED POINTS OF A VERTICALLY-DISPOSED ELONGATED REACTOR

BACKGROUND OF THE INVENTION

The present invention relates to a catalytic alkylation process and apparatus. In a more specific aspect, the present invention relates to a catalytic alkylation process in which an alkylatable hydrocarbon is contacted with an alkylating agent in the presence of an acid-type catalyst and the catalyst is cyclically circulated through the system. In yet another aspect, the present invention relates to a catalytic alkylation process and apparatus in which an acid-type catalyst is cyclically circulated through the system to produce an alkylate product of improved octane number.

Numerous processes are known in the prior art for alkylating an alkylatable hydrocarbon with an alkylating agent in the presence of a catalyst. From a commercial standpoint, the most prevalent systems involve the cyclic circulation of an acid-type catalyst, such as hydrofluoric acid, sulfuric acid, etc. through a reaction zone, a separation zone, a cooling zone and back to the reaction zone.

One such process for the alkylation of hydrocarbons, utilizing the cyclic circulation of the catalyst, introduces the reactant hydrocarbons in a gaseous phase. In this system the gaseous hydrocarbon feed mixture is introduced at a high velocity to the lower portion of the reaction zone and into a continuous catalyst phase maintained in the reaction zone. Suitable conditions of temperature and residence or contact time are provided in the reaction zone whereby the alkylatable hydrocarbon is alkylated. An effluent stream comprising catalyst, alkylate product and unconsumed reactants passes from the upper portion of the reaction zone into a settling zone, wherein separation occurs between the alkylate product phase and the catalyst phase. The alkylate product phase is withdrawn from the settling zone for further processing, as by fractionation, and the catalyst phase is passed downwardly to a cooling zone and thence back into the reaction zone.

Another process, based on the cyclic circulation of the catalyst, which overcomes certain of the inherent deficiencies of the gas phase process and permits operation at low reaction temperatures, introduces the reactant hydrocarbons in the liquid phase. In this process, the hydrocarbon reactants are introduced into the bottom of the reaction zone through constricted passageways, thereby creating a liquid lift system, whose motive power comes from the difference in density of the flowing streams and to some extent from the kinetic energy of the inlet hydrocarbon stream, and at the same time creating small droplets of reactants having a high interfacial area which result in a desirably high reaction rate. The reactant hydrocarbons and catalyst move upwardly through an elongated, tube-type reaction zone, the effluent, including alkylate product, catalyst and unreacted hydrocarbons, is discharged from the reaction zone into a settler-surge vessel, an alkylate product phase is withdrawn for further processing and a catalyst phase is passed downwardly through a tube-type conduit to a cooler and thence back into the reaction zone.

It has been recognized in the art that an alkylate product of improved octane number can be produced by operating at low temperatures and as the temperature of the reaction is lowered, the octane number of the alkylate product will increase. Consequently, it has become the practice in the prior art to operate at the lowest possible reaction temperature commensurate with the recognition of the economics involved, the feed materials utilized, the speed of the reaction, the percent conversion and other factors.

It has also been recognized that optimum conditions, particularly temperature, are dependent to a great extent upon the feed materials utilized. Consequently, it has been the practice of the prior art, when a plurality of alkylating agents are used, to operate a plurality of alkylation systems in parallel in order to utilize optimum conditions for each particular feed material. Obviously, such duplication of equipment is expensive, difficult to control and prone to produce alkylate products of varying character. Such parallel operating procedures are further complicated by the number of feed material streams available in refineries, particularly streams of alkylating agents, the variety of different treatments to which such streams are subjected and, more recently, changes in the character of crude oils available to the refinery.

It would therefore be highly desirable if a process could be provided which would eliminate the duplication of certain equipment, permit the alkylation of each feed under optimum conditions, which would be inexpensive to install and operate, which would be flexible in operation in order to accommodate a wide variety of different feed materials and which would produce an alkylate product of essentially constant, high quality.

It has also been recognized in the art that in order to obtain an alkylate product of maximum octane number, the weight percent total acidity of the catalyst should not exceed a given amount. While the tolerable acidity of the catalyst will vary depending upon the reactant hydrocarbons and the temperature of operation, it is generally thought that the total acidity of the catalyst under any conditions should not be higher than about 90 percent, that alkylate products of highest octane number are obtained at acidities substantially lower than this and, consequently, that the weight percent total acidity of the catalyst for optimum octane number should be between about 87 percent and 67 percent. Consequently, the catalyst is in some way diluted so as to maintain the desired total acidity. Obviously, water would be the logical diluting agent to utilize. However, the presence of excessive amounts of water, in systems utilizing acid catalysts, creates problems in that, in conjunction with the acid, water is highly corrosive to the alkylation system and catalyst handling system. Therefore, the acid catalyst is normally utilized in an essentially anhydrous condition. There is a tendency in alkylation systems for water to accumulate as the result of its presence in the hydrocarbon reactants and its absorption from the atmosphere. Therefore, alkylation systems employing acid-type catalysts normally include a so-called catalyst "rerun" system through which catalyst is at least periodically passed in order to remove water therefrom. The rerun system will normally involve withdrawing a portion of the catalyst phase as it flows from the separator to the cooler. The withdrawn catalyst phase is heated to a temperature sufficient to vaporize residual alkylate, unreacted hydrocarbons, and the major part of the acid phase from the water. Water, together with some acid-soluble oil, is withdrawn as a bottoms product from the rerun separator while the vapor phase is recycled to the settler-surge zone or back to the separated acid phase. Generally, a portion of the alkylatable hydrocarbon, in liquid form, is utilized as a reflux and another portion, in gaseous form, as a stripping medium in the rerun separator.

It is also recognized in the art that a certain amount of dilution of the catalyst phase inherently occurs in the reaction zone itself. Specifically, what is known as a catalyst- or acid-soluble oil (ASO) is produced in the reaction zone, which inherently acts as a diluent for the catalyst phase. While the specific nature of the acid-soluble oil has not been completely established, it is generally accepted that it comprises predominantly polymeric materials with minor amounts of complexes and small or trace amounts of impurities, such as sulfur, to the extent such impurities exist in the alkylation feed materials. These catalyst-soluble oils are retained in the catalyst phase during the separation of the alkylate phase from the catalyst phase and consequently are recycled to the alkylation system. It has also been universally accepted, by those skilled in the art, that the production of catalyst-soluble oil is substantially in excess of that necessary or desirable for dilution of the catalyst. Consequently, the prior art contains suggestions for the removal of the excess catalyst-soluble oil.

Finally, those skilled in the art have recognized the fact that under normal operating conditions the production of catalyst-soluble oils is extremely slow. Accordingly, the prior art has suggested various start-up procedures which will rapidly produce the desirable inventory of catalyst-soluble oil, thereby substantially shortening the time necessary to arrive at full-scale production of alkylate product.

Accordingly, it would also be highly desirable if a simple and inexpensive process could be provided wherein the degree of catalyst dilution could be closely controlled and maintained at optimum levels while at the same time controlling the amount of water present in the catalyst.

It would also be highly desirable to provide means for substantially shortening the necessary start-up period and for thereafter maintaining a predetermined amount of catalyst-soluble oil in the catalyst system.

It is therefore an object of the present invention to provide an improved system for the alkylation of hydrocarbons. Another and further object of the present invention is to provide an improved system for the alkylation of hydrocarbons, utilizing a cyclic flow of an acid-type catalyst. A further object of the pesent invention is to provide an improved system for the alkylation of hydrocarbons, utilizing a cyclic flow of an acid-type catalyst, in which an alkylate product of improved octane number is obtained. Another and further object of the present invention is to provide an improved system for the alkylation of hydrocarbons wherein duplication of equipment is substantially reduced. A still further object of the present invention is to provide an improved system for the alkylation of hydrocarbons in which feed materials of different characters can be reacted under optimum conditions for each feed. Still another object of the present invention is to provide an improved system for the alkylation of hydrocarbons in which the initial cost as well as the operating costs are significantly lowered. Yet another object of the present invention is to provide an improved system for the alkylation of hydrocarbons which is flexible and thus able to accommodate different feed materials without changes in the system. Yet another object of the present invention is to provide an improved system for the alkylation of hydrocarbons, utilizing a cyclic flow of an acid-type catalyst, in which the acid-soluble oil content of the catalyst phase is maintained within a predetermined critical range. Another and further object of the present invention is to provide an improved system for the start-up of a system for the alkylation of hydrocarbons, utilizing cyclic flow of an acid-type catalyst. These and other objects and advantages of the present invention will be apparent from the following detailed description of the invention.

SUMMARY OF THE INVENTION

A method of alkylating an alkylatable hydrocarbon with different alkylating agents, at different reaction temperatures and in a single reaction zone, in which an alkylatable hydrocarbon is contacted with an acid-type catalyst and different alkylating agents at different points in an elongated reaction zone, the reaction zone effluent is separated into a hydrocarbon phase and a catalyst recycle phase and the different reaction sections of the reaction zone are maintained at different temperatures by splitting the recycle catalyst phase into an equal number of streams and adjusting the temperatures in the reaction sections by adjusting the temperatures of the recycle catalyst streams, the relative volume of the recycle catalyst phase streams or both.

Inasmuch as there is some confusion of terminology in the art as to which of the reactants is the alkylatable hydrocarbon and which is the alkylating agent, an isoparaffin hydrocarbon, when referred to herein, will be referred to as the "alkylatable hydrocarbon" while an olefinic hydrocarbon will be referred to herein as the "alkylating agent".

DESCRIPTION OF THE PREFERRED EMBODIMENTS

While, as previously indicated, the present invention can be carried out in any type of reactor system utilizing a cyclically flowing, acid-type catalyst, the preferred system, in accordance with the present invention, is a cyclic catalyst system in which the mixture of hydrocarbon feed materials is maintained in a liquid state. Such a system is described in detail in U.S. Pat. No. 3,213,157, which is incorporated herein by reference. Briefly, the system comprises a vertically-disposed tubular reactor into which a mixture of the hydrocarbon feed materials and the catalyst are introduced, a horizontally-disposed settler-surge vessel, adapted to receive effluent from the top of the reactor and separate the effluent into liquid alkylate product phase, which is further processed by fractionation or the like, and a liquid catalyst phase and a vertically-disposed tubular catalyst return conduit through which the catalyst phase passes downwardly and is then recycled to the reactor. This entire system is in open communication throughout for cyclic catalyst flow. Normally, catalyst phase is at least periodically withdrawn from the separated catalyst phase conduit and passed to a heater where it is heated to a temperature sufficient to cause separation of a liquid phase, comprising predominantly water and some catalyst-soluble material, and a vapor phase comprising predominantly catalyst, unreacted feed materials and some alkylate. The heated catalyst phase is then passed to a rerun column, which is normally operated with a liquid portion of the alkylatable hydrocarbon, as a reflux, and a vapor portion, as a stripping agent. The vapor phase product of the rerun column is then returned to the system's settler-surge vessel or back to the catalyst phase at a point below the point at which catalyst phase was withdrawn for rerun or is further fractionated to obtain a separated rerun catalyst and a separated recycle alkylatable hydrocarbon, while the water, and any catalyst-soluble material present, is withdrawn as a liquid phase and discarded.

Conventionally, the alkylation reaction can comprise the reaction of an isoparaffin with an olefin or other alkylating agent, reaction of a normal paraffin with an olefin or other alkylating agent or the reaction of an aromatic hydrocarbon with an olefin or other alkylating agent. However, where gasoline blending stocks are to be produced, the reaction generally involves reaction of an isoparaffin, such as isobutane, with $C_3$ or higher monoolefins, such as propylenes and butenes, such as isobutylene, butene-1 and/or butene-2's. Therefore, a preferred embodiment of present invention is directed to a reaction involving these specified materials and mixtures thereof. One preferred olefinic mixture is a mixed "butenes" product from a catalytic cracking operation, which will comprise about 25.0% by volume of butene-1, about 30.0% by volume of isobutylene and about 45.0% by volume of butene-2's.

A variety of alkylation catalysts can be employed in the alkylation reaction, including well known acid catalysts such as sulfuric acid, hydrofluoric acid, phosphoric acid; metal halides, such as aluminum chloride, aluminum bromide, etc.; and other alkylation catalysts. A preferred catalyst for use in the present invention is hydrofluoric acid.

The reaction may be carried out at pressures varying from atmospheric to as high as 1000 psi and higher, preferably about 125 to 220 psia, and at residence times of 20 seconds to 5 minutes. The pressure is preferably sufficient to maintain the hydrocarbon reactants in their liquid phase.

In an alkylation reaction, involving the alkylation of isoparaffins with olefins, a substantial molar excess of isoparaffin to olefin is employed to provide a feed ratio in excess of 1/1, usually about 4/1 to about 70/1 and preferably about 5/1 to about 20/1.

As previously indicated, the reaction zone is preferably maintained under sufficient pressure to insure that the hydrocarbon reactants and the alkylation catalyst are in a liquid phase. The temperature of the reaction will vary with the reactants and with the catalyst employed but generally ranges from between about $-40°$ F. to about 150° F. However, it has been found, in accordance with the present invention, that alkylates of optimum octane number are obtained by alkylating isobutane with propylene at a temperature between about 80° and about 120° F., preferably about 100° F., and alkylating isobutane with a butenes mixture at a temperature between about 40° and about 90° F. Preferably, the upper ranges are used so that cooling water from a cooling tower can be used, thus eliminating costly refrigeration. It has also been found, in accordance with the present invention, that different alkylating agents can be utilized to alkylate one or more alkylatable hydrocarbons at optimum conditions for the particular alkylating agent in a single reactor. Maintenance of the optimum reaction temperature for a particular alkylating agent in a single reactor is accomplished by separately introducing each of the different alkylating agents at different points along the reaction zone, splitting the recycle catalyst phase into an equal number of streams and adjusting the reaction temperature for each alkylating agent by controlling the volume of recycle catalyst phase introduced adjacent the point of introduction of each olefinic alkylation agent and/or adjusting the temperature of each of the separate streams of recycle catalyst phase.

The preferred amount of catalyst-soluble oil built up in the catalyst phase during startup and maintenance of the alkylation reactions should be between about 0.4 and about 8.0 weight percent of the total catalyst phase and even more density between about 0.5 and about 6.0 weight percent. The water content of the catalyst phase should be between about 0.5 and about 5.0 weight percent of the total catalyst phase, preferably below about 2.0 weight percent and still more desirably below about 1.5 weight percent. The total catalyst-soluble oil and water should be between about 0.9 and about 25 weight percent of the total catalyst phase, preferably between about 0.9 and about 12 weight percent and still more desirably between about 3 and about 6 weight percent. Finally, the acidity of the catalyst phase should be between about 70 and about 90 weight percent of the catalyst phase and preferably between about 85 and about 90 weight percent. The difference between the acid content of the catalyst phase and the total of the catalyst-soluble oil and water will generally be a portion of the isoparaffin feed which has been dissolved in the catalyst phase.

As indicated, the catalyst is most effective and produces products of highest octane number if the catalyst is diluted to produce a catalyst phase having the previously specified total acidity. Consequently, diluents should be present or added to the catalyst phase. As previously indicated, natural diluents are present in the catalyst phase after some period of operation. However, it is undesirable to maintain water as a diluent because of its highly corrosive character in combination with the acid and other factors such as a reduction in the quality of the product. Consequently, a catalyst-soluble oil normally built up in the acid phase during operation is quite effective and has been found to be a desirable diluent. While in some instances, depending upon the character of the alkylating agent, sufficient catalyst-soluble oil is built up in the catalyst phase, in other instances, there is a net loss of catalyst-soluble oil or an insufficient amount produced under normal conditions. This is particularly true when the catalyst phase is rerun to remove water since a certain amount of catalyst-soluble oil is removed during the removal of the water. In addition, certain alkylating agents such as butylene in a butenes mixture does not form sufficient catalyst-soluble oil to maintain the inventory of catalyst-soluble oil at the desired level. Propylene and mixtures containing the same produce somewhat larger amounts of catalyst-soluble oils but due to the loss of catalyst-soluble oil during rerun of a caralyst phase, the ability of a propylene feed to produce sufficient catalyst-soluble oil becomes borderline. In addition, when propylene is utilized in a combination process such as the present process where butylenes are also utilized, insufficient catalyst-soluble oil will be produced to maintain both reactions. Further, when operating at lower temperatures as are preferred herein, the amount of catalyst-soluble oil produced will also be reduced. On the other hand, $C_5$ and higher monoolefins such as amylenes, hexenes, etc., produce substantial quantities of catalyst-soluble oils and normally more than would be necessary. Still larger amounts are produced by diolefins such as butadiene. Therefore, in accordance with one aspect of the present invention, the amount of catalyst-soluble oil present in the catalyst phase is at least periodically determined and $C_3$ or $C_5$ and higher monoolefins, diolefins or mixtures thereof are added to the catalyst phase in order to generate additional catalyst-soluble oil and make up any deficiency detected.

In yet another aspect of the present invention, the generation of catalyst-soluble oil can be improved by heating a part of propylene feed, where one of the feed materials is propylene, or $C_3$ or $C_5$ monoolefins or diolefins from an outside source to a temperature significantly above the temperature of the catalyst phase. At this higher temperature, catalyst-soluble oil is generated more rapidly and in greater quantities. For example, the catalyst phase may be normally between about 70° and 115° F. If the $C_3$ or $C_5$ and higher monoolefins or diolefins or mixtures thereof are heated to temperatures between about 160° and 215° F., preferably about 170° F. and then added to the catalyst phase, the temperature of the combined catalyst phase and the heated olefins will be between about 140° and 160° F. and preferably about 150° F. At this temperature catalyst-soluble oil is produced in significant amounts and more rapidly than under normal system conditions.

Yet another alternative for maintaining the catalyst-soluble oil inventory at the desired level, in accordance with another embodiment of the present invention, is to generate the catalyst-soluble oil in a reaction separate from the alkylation system. Specifically, a portion of the propylene feed or an outside source of $C_3$ or $C_5$ and higher monoolefins or diolefins is fed to a reactor along with a portion of acid catalyst. The acid catalyst may be fresh catalyst, a portion of the rerun catalyst or a portion of the separated catalyst phase. For obvious reasons, fresh catalyst is preferred. By utilizing a catalyst-:olefin ratio of about 0.5 to about 5.0, a reaction temperature of about 50° to 150° F., a pressure of about 50 to 200 psia (liquid phase) and a batch reaction time of about 5 to 60 minutes, catalyst-soluble oil can be effectively and rapidly formed. Thereafter, the generated catalyst-soluble oil is added to the recycle catalyst phase in accordance with any detected deficiencies in the catalyst-soluble oil content of the recycle catalyst phase.

The previously described techniques for maintaining and generating catalyst-soluble oil are also most helpful in reducing the time necessary for the startup of an alkylation reaction.

Conventionally, the system is lined out by first introducing a dried isoparaffinic hydrocarbon to the unit and passing it continuously through the alkylation reactor, the settler, and the isoparaffin stripper and then recycling the same to the alkylation reactor in order to dry out the alkylation apparatus before fresh, essentially anhydrous hydrofluoric acid is introduced. Generally, drying of the feed is accomplished by passing the isoparaffin through molecular sieve dryers or other drying means well known in the art. The dried isoparaffin is then continuously charged to the unit until a rate of continuous recycle equal to the rate of recycle during normal operation is attained. After it has been determined that the alkylation is sufficiently dry and the isoparaffin recycle rate has been established, hydrofluoric acid is charged to the alkylation apparatus and continuously circulated through the reactor, the settler, the cooler and back to the reactor. This circulation continues until the desired normal circulation rate of hydrofluoric acid is attained. Thereafter, the olefinic feed material is introduced into the reactor and continuous operation is commenced.

The present invention will be further illustrated by referring to the accompanying drawings which show certain of the preferred embodiments of the invention.

Figure 1:
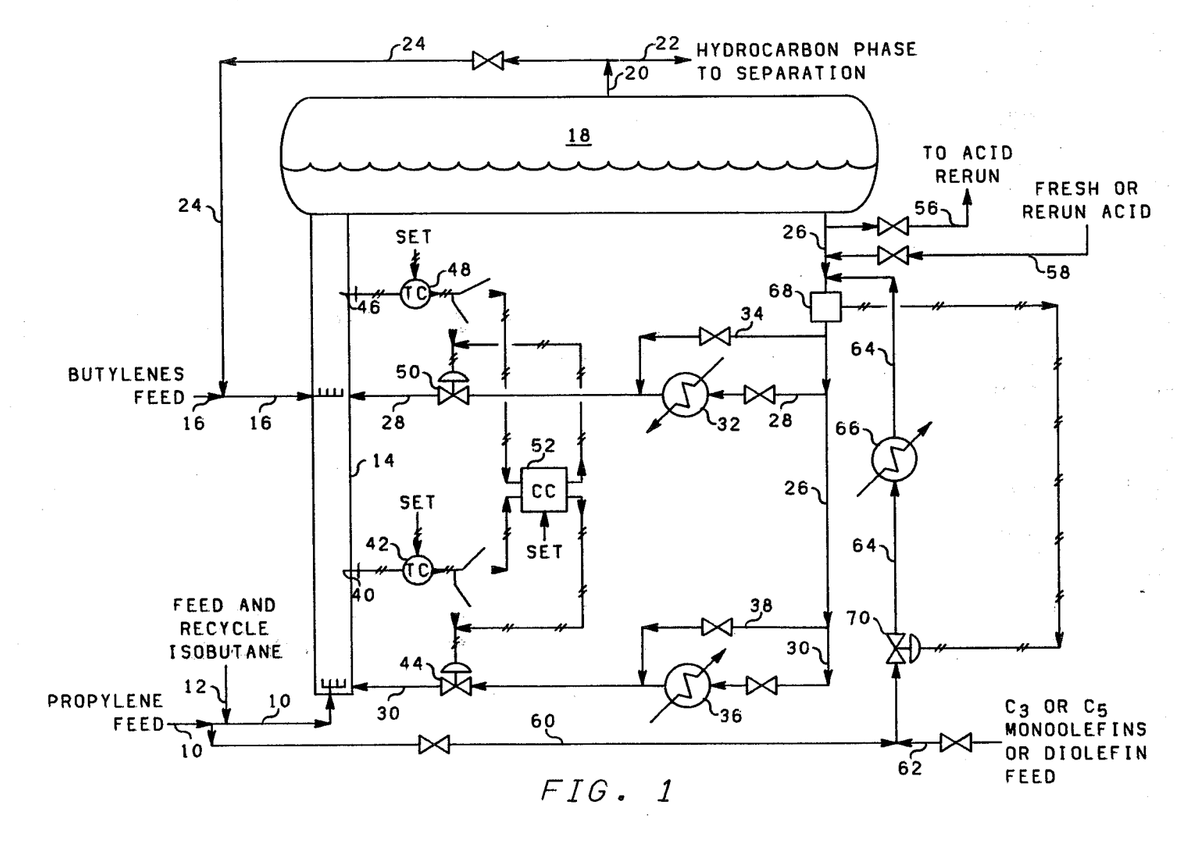
FIG. 1 is a simplified flow diagram of an alkylation system in accordance with one embodiment of the present invention.

In accordance with FIG. 1, a feed rich in propylene is fed to to the system through line 10 while isobutane or another alkylatable hydrocarbon is added through line 12. The isobutane may be from an outside source or from an outside source plus recycle isobutane recovered from the alkylation product. The mixture of propylene and isobutane is passed upwardly into a vertically disposed tube-type reactor 14. Downstream from the point of introduction of the propylene feed a feed rich in butylenes is fed into the reactor. The reactants pass upwardly through reactor 14 in admixture with the catalyst as will be hereinafter explained. Reaction product from the effluent upper end of reactor 14 passes into surge-separator 18. Surge-separator 18 is preferably a horizontally-disposed separator in which the effluent separates into a liquid hydrocarbon product phase and a liquid catalyst phase. The hydrocarbon product phase is withdrawn through line 20 and passed through line 22 to a hydrocarbon product phase separation system not shown. The hydrocarbon phase separation system separates (usually by distillation) the alkylate product from unreacted isobutane, propane, normal butane, and residual amounts of acid. In a preferred embodiment of the present invention, a portion of the hydrocarbon product phase is passed through line 24 and is combined with the butylenes feed passing through line 16 and is thence passed to the reactor 14. When recycling a portion of the hydrocarbon product phase, the recycled portion acts as a diluent for the butylenes feed, thus inhibiting polymerization reactions in the reactor, and increases the isobutane-to-butylenes feed ratio, since the recycle hydrocarbon is rich in isobutane. The separated acid phase is withdrawn from separator 18 through line 26 and is ultimately recycled to the reactor. In accordance with the present invention, the recycled catalyst phase passing through line 26 is split into two separate streams. A first stream is passed through line 28 to the reactor at a point adjacent the point of introduction of the butylenes feed while a second portion is passed through line 30 to reactor 14 and is introduced at a point adjacent the point of introduction of the propylene feed. Since the butylenes reaction is conducted at a low temperature, in some instances recycled catalyst phase will be cooled by means of cooler 32, or alternatively it can be passed directly to the reactor through line 34. The cooling means 32 may be an absorption type refrigeration unit utilizing waste heat from the process itself or may be a water-cooled heat exchanger. To the extent necessary or desirable, the portion of the recycle catalyst phase fed to the bottom portion of the reactor is passed through heat exchanger 36 where it is heated to a desired temperature or through bypass line 38 which bypasses the heater. Under normal operations, with the propylene and butylene feeds as indicated, only cooling means 32 would be utilized, since the recycled catalyst will be at the proper temperature for introduction to the higher temperature portion of the reactor, since alkylation is an exothermic process. In order to maintain the reaction temperatures at optimum levels within the reactor the temperature is measured at a point above the point of introduction of the propylene, and at which the reaction temperature has become stabilized, by means of temperature detector 40. The detected temperature signal is transmitted to temperature controller 42 which in turn operates valve 44 in line 30. Accordingly, by controlling valve 44 and thus the rate of flow of recycled catalyst through line 30, the amount of recycled catalyst passing through line 28 is also controlled so that, in the end, by properly adjusting the proportion of recycled catalyst passing through lines 28 and 30, respectively, optimum reaction temperatures may be maintained for the propylene reaction and the butylenes reaction, respectively. Where only two recycled catalyst streams are utilized, a single temperature measurement, as indicated, will normally be adequate. However, for more precise control, the temperature can also be measured at a point above the point of introduction of butylenes feed, and at which the butylenes reaction has become stabilized, by means of temperature detector 46. The signal from detector 46 is passed through temperature controller 48 which in turn controls valve 50 in line 28. Still more precise control may be attained by feeding the signals from temperature controllers 42 and 48 to computer controller 52 which in its simplest form would be a ratio controller. The ratio controller 52 would then have its output signals fed to valves 44 and 50, respectively, to thereby control the ratio of recycle catalyst phase passing through lines 28 and 30, respectively. The arrangement utilizing computer controller 52 would of course be necessary where more than two olefin feeds are utilized and thus more than two recycle catalyst streams are utilized. It would of course be obvious that the butylenes feed could be introduced at the bottom of the reactor 14 while the propylene feed is introduced upstream. In this case, it would also be obvious to place cooling means 32 in line 30 and heater 36 in line 28. As previously indicated, a certain portion of the catalyst recycle phase should at least periodically be removed as through line 56 and passed to acid rerun system for the removal of contaminants, particularly water and some acid-soluble oil. The rerun acid or fresh acid, as needed, would be introduced to the system through line 58.

In order to effectively and rapidly build up the desired inventory of catalyst-soluble oil in the alkylation system, at least a portion of the propylene feed is passed through line 60 or $C_3$ or $C_5$ and higher monoolefins or diolefins from an outside source are fed through line 62. These olefinic feeds then pass through line 64 and are heated, as previously indicated, by means of heater 66. The heated olefinic materials are then combined with the circulating catalyst in line 26 where they react at the elevated temperature to produce catalyst-soluble oil. Obviously, this means may be utilized to make up any deficiencies of catalyst-soluble oil during normal operation of an alkylation system and thus maintain the desired inventory of catalyst-soluble oil in the system. During either startup or normal operation of a system, the amount of catalyst-soluble oil in a recycled acid phase may be at least periodically or continuously detected by means of detector controller means 68. Detector controller means 68 will send a signal related to the amount of catalyst-soluble oil in the recycled catalyst phase to a control valve 70 in line 64 to thus control the volume of olefinic materials added to the alkylation system through heater 66.

Figure 2:
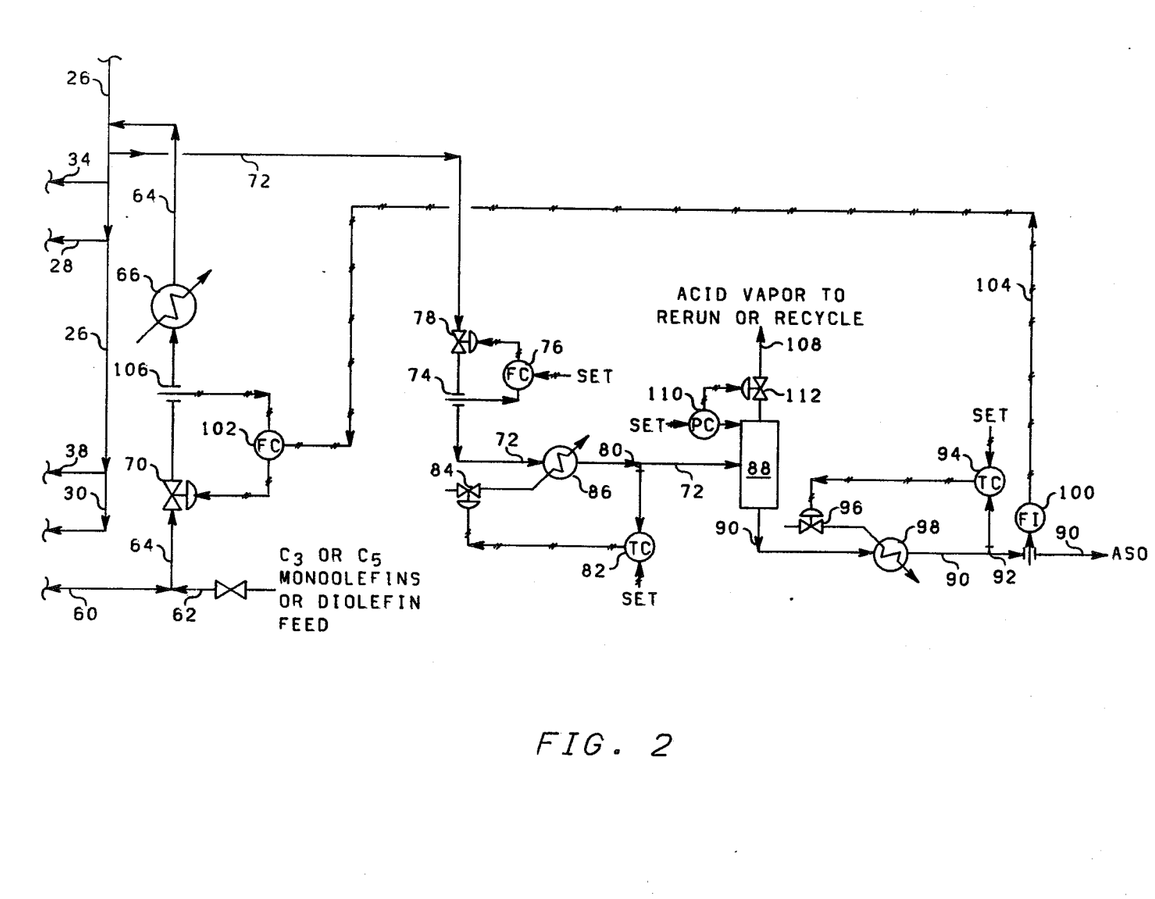
FIG. 2 is a more detailed diagram of a control means for the system of FIG. 1.

The control system comprising detector controller 68 and control valve 70 is shown in somewhat greater detail in FIG. 2 of the drawings. In accordance with FIG. 2, a small slip stream of separated acid phase is withdrawn through line 72. The volume of this slip stream is controlled by flow indicator 74 in combination with flow controller 76 and control valve 78. Flow controller 76 is set at a predetermined flow by the operator. The temperature of the withdrawn sample stream, passing through line 72 is also measured by means of temperature indicator 80. The measured temperature is transmitted to temperature controller 82 and a control signal is transmitted to valve 84 which controls the volume of heating medium to heater 86. Temperature controller 82 is set so as to heat a sample of the acid phase in line 72 to a temperature sufficient to remove all acid and water as a vapor and leave the remaining acid-soluble soluble oil as a liquid bottoms product in separator 88. From separator 88, the unvaporized catalyst-soluble oil is discharged through line 90. Inasmuch as the volume of the catalyst-soluble oil is so small, it can be discarded without having any impact on the overall alkylation operation. The catalyst-soluble oil in line 90 may be temperature controlled by the combination of temperature indicator 92, temperature controller 94 and valve 96 on the coolant line to cooler 98. The volume of catalyst-soluble oil in line 90 is measured by flow indicator 100 which sends a signal or set point to flow controller 102 through line 104. The flow through line 64 is measured by flow indicator 106. The flow measured by indicator 106 is transmitted to flow controller 102 which in turn controls the flow through valve 70. Flow controller 102 may include a ratio controller or add or substract circuit means. The separated vapor phase from separator 88 is discharged through line 108 and discarded or it may be recycled to the catalyst system or passed to the catalyst rerun system. The pressure in separator 88 is controlled by pressure controller 110 and control valve 112.

Figure 3:
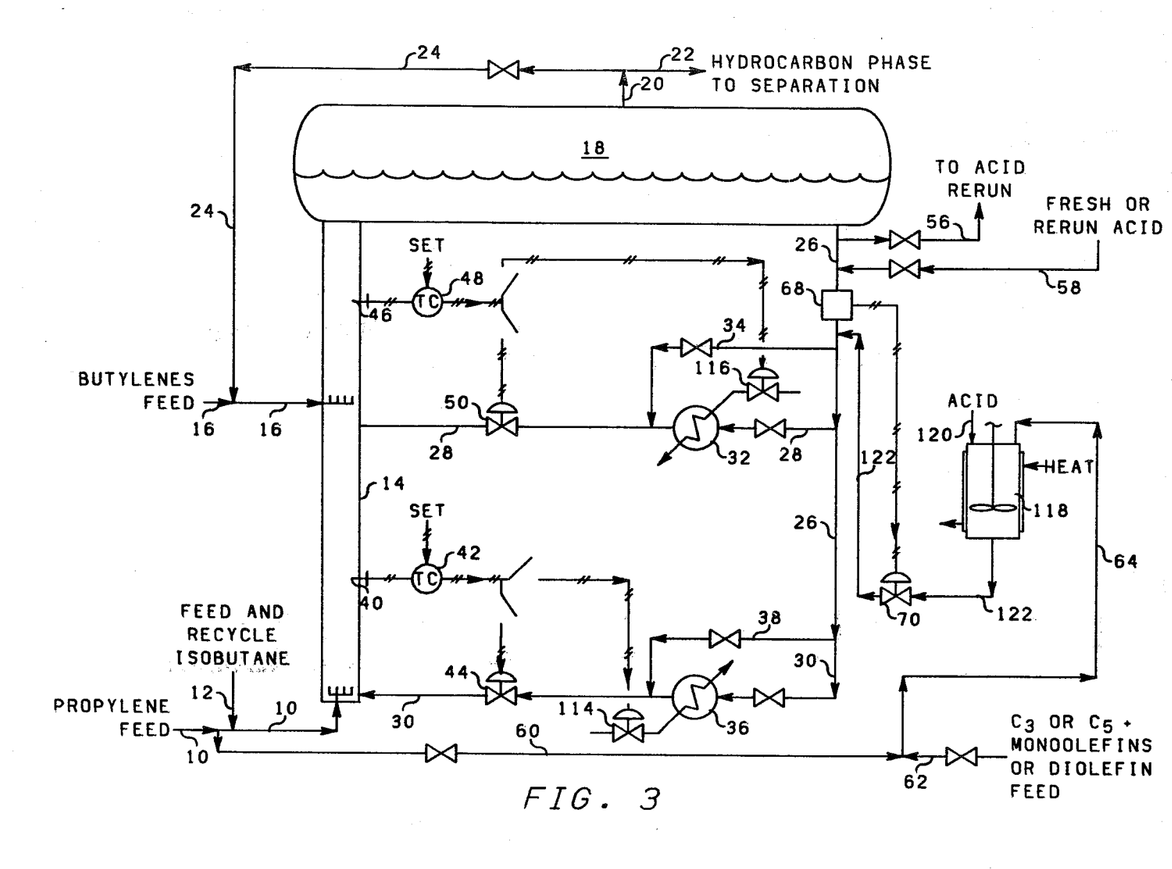
FIG. 3 is a simplified flow diagram of a second embodiment of the present invention.

FIG. 3 of the drawings shows another embodiment of the present invention. FIG. 3 shows substantially the same overall alkylation system as that shown in FIG. 1 and, accordingly, like numbers have been utilized in FIG. 3 to designate like elements which correspond to those of FIG. 1.

However, FIG. 3 shows an alternative or additional control system for controlling the reaction temperatures within reactor 14. Specifically, temperature controller 42 can control flow valve 44, as previously described with respect to FIG. 1, to thereby control the rate of flow of recycle catalyst phase introduced into the reactor 14 through line 30. Alternatively, or in addition to this control, the signal from temperature controller 42 may be utilized to control the temperature of heater 36. This is accomplished by transmitting the signal from temperature controller 42 to control valve 114 mounted in the line supplying heating medium to heater 36. Likewise, instead of or in addition to the control of valve 50 in line 28 by means of the signal from temperature controller 48, the temperature control signal can be passed to control valve 116 mounted in the line supplying cooling medium to cooling means 32. Thus, the split between the volume of recycle catalyst phase passing through lines 28 and 30, respectively, may be maintained constant throughout, at predetermined values which will generally maintain the appropriate reaction temperatures at points 40 and 46 in reactor 14. However, additional temperature control can be attained by adjusting the temperature of the recycle catalyst phase streams passing through lines 28 and 30, respectively, by adjusting the cooling and heating thereof by means of cooler 32 and heater 36, respectively. It is of course obvious that the proportions or ratio of recycled catalyst phase passing though lines 28 and 30, respectively, can be controlled continuously by control valves 50 and 44, respectively, and such control can be augmented by controlling the temperature of the recycled catalyst phase passing through lines 28 and 30 by control valves 116 and 114, respectively, which control cooler 32 and heater 36, respectively.

FIG. 3 also illustrates an alternative to the use of heater 66 (of FIG. 1) to generate and add catalyst-soluble oil to the alkylation system. In accordance with FIG. 3, feed propylene or $C_3$ or $C_5$ and higher monoolefins or diolefins from an outside source passing through line 64 are supplied to a heated, externally-disposed reactor 118. Acid, which may be fresh, rerun or separated acid phase, is introduced to reactor 118 through line 120. Catalyst-soluble oil produced in reactor 118 is discharged through line 122 and passed to catalyst recycle line 26 where it is added to the separated recycle phase. The control system utilized for controlling the addition of catalyst-soluble oil to the recycle catalyst phase, comprising detector controller 68 and control valve 70, can be basically the same as that illustrated and described with respect to FIG. 2.

While specific examples of materials, equipment and procedures have been referred to herein for purposes of illustration, it is to be understood that such recitations are not to be considered limiting but alternative substitutes and equivalents thereof will be obvious to one skilled in the art.

What is claimed is:

1. A method of alkylating at least one alkylatable hydrocarbon with at least two different alkylating agents and an equal number of different reaction temperatures, respectively, in a single reaction zone and in the presence of an acid-type catalyst, comprising:
   introducing a first alkylating agent, at least a portion of at least one alkylatable hydrocarbon and an acid-type catalyst at a first point adjacent the lower end of a vertically-disposed, elongated alkylation reaction zone and passing the same upwardly through said reaction zone;
   introducing at least one other alkylating agent, differing from said first alkylating agent and from one another, into said reaction zone at at least one spaced, other point, above said first point and passing the same upwardly through said reaction zone;
   passing effluent from the upper, discharge end of said reaction zone into a separation-surge zone;
   separating said effluent into a hydrocarbon product phase and an acid phase in said separation-surge zone; and
   maintaining different reaction temperatures adjacent each of said first point and said at least one other point by dividing the thus separated acid phase into a number of recycle acid phase streams equal to the number of said first point and said at least one other point and recycling one of said recycle acid phase streams to said reaction zone adjacent said first point and recycling each of said other streams of said number to said at least one other point respectively.

2. A method in accordance with claim 1 wherein the different reaction temperatures are maintained by adjusting at least one of the volumetric flow of at least one of the recycle acid phase streams or the temperature of at least one of said recycle acid phase streams.

3. A method in accordance with claim 1 wherein two different alkylating agents are utilized, including a first and a second alkylating agent, the separated acid phase is divided into two recycle acid phase streams, including a first and a second recycle acid phase streams, and two different reaction temperatures are maintained including a first and a second reaction temperature.

4. A method in accordance with claim 3 wherein the two different reaction temperatures are maintained by adjusting at least one of the volumetric flow of said first recycle acid phase stream, the volumetric flow of said second acid phase stream, the temperature of said first recycle acid phase stream or the temperature of said second recycle acid phase stream.

5. A method in accordance with claim 4 wherein the volumeric flow of the first recycle acid phase stream and the second recycle acid phase stream are adjusted.

6. A method in accordance with claim 5 wherein the volumetric flow of the first recycle acid phase stream and the second recycle acid phase are adjusted by determining the reaction temperature at a point above at least one of the point of introduction of the first alkylating agent or the point of introduction of the second alkylating agent, at which said respective reaction temperatures have become stabilized, and adjusting the volumetric flow of that one of said first recycle acid phase stream and said second recycle acid phase stream which is introduced adjacent the point at which said reaction temperature was measured.

7. A method in accordance with claim 6 wherein the lower of the two reaction temperatures is measured and the volumetric flow of the recycle acid phase stream introduced adjacent said point at which said lower reaction temperature is measured is adjusted.

8. A method in accordance with claim 6 wherein the temperature is measured at a point above and adjacent the point of introduction of the first alkylating agent and the volumetric flow of the first recycle acid phase stream is adjusted.

9. A method in accordance with claim 5 wherein the reaction temperature is measured at a point above each of the point of introduction of the first alkylating agent and the point of introduction of the second alkylating agent, at which said respective reaction temperatures have become stabilized, and the volumetric flows of both the first recycle acid phase stream and the second recycle acid phase stream are adjusted.

10. A method in accordance with claim 4 wherein at least one of the first recycle acid phase stream and the second recycle acid phase stream are cooled prior to the introduction thereof into the reaction zone.

11. A method in accordance with claim 10 wherein the reaction temperature is determined at a point above at least one of the point of introduction of the first alkylating agent or the point of introduction of the second alkylating agent, at which said respective reaction temperature has become stabilized, and the temperature at which that recycle acid phase stream introduced into the reaction zone adjacent the point at which said reaction temperature was measured is adjusted to maintain said reaction temperature at a predetermined value.

12. A method in accordance with claim 4 wherein that recycle acid phase stream introduced into the reaction zone adjacent the point at which the higher of the two different reaction temperatures is to be maintained is heated.

13. A method in accordance with claim 12 wherein the reaction temperature is determined at a point above the point at which the higher reaction temperature of the two different reaction temperatures is to be maintained and the temperature of that recycle acid phase stream introduced into the reaction zone adjacent the point at which said higher reaction temperature is measured is adjusted to maintain said higher reaction temperature at a predetermined level.

14. A method in accordance with claim 4 wherein that recycle acid phase stream which is introduced adjacent the point at which the lower of the two different reaction temperatures is to be maintained is cooled.

15. A method in accordance with claim 14 wherein the reaction temperature is determined at a point above the point at which the lower of the two different reaction temperatures is to be maintained and the temperature of that recycle acid phase stream introduced into the reaction zone adjacent the point at which said lower reaction temperature is measured is adjusted to maintain said lower reaction temperature at a predetermined level.

16. A method in accordance with claim 4 wherein that recycle acid phase stream introduced adjacent the point at which the lower of the two reaction temperatures is to be maintained is cooled and that recycle acid phase stream introduced into the reaction zone adjacent the point at which the higher of said two different reaction temperatures is to be maintained is heated.

17. A method in accordance with claim 16 wherein the reaction temperatures are determined at a point above the point of introduction of the first alkylating agent and at a point above the point of introduction of the second alkylating agent, at which said respective reaction temperatures have become stabilized, the temperature to which the heated recycle acid phase is heated is adjusted to maintain a predetermined temperature in the higher temperature one of the two reaction zones and the temperature to which the cooled recycle acid phase is cooled is adjusted to maintain a predetermined temperature in the lower temperature one of said two reaction zones.

18. A method in accordance with claim 1, 2, 3, 4, 5, 6, 7, 8, 9, 10, 11, 12, 13, 14, 15, 16 or 17 wherein a portion of the separated hydrocarbon product phase is recycled to at least one of the point of introduction of the first alkylating agent and the point of introduction of the second alkylating agent.

19. A method in accordance with claim 1, 2, 3, 4, 5, 6, 7, 8, 9, 10, 11, 12, 13, 14, 15, 16 or 17 in which the alkylatable hydrocarbon is isobutane.

20. A method in accordance with claim 1, 2, 3, 4, 5, 6, 7, 8, 9, 10, 11, 12, 13, 14, 15, 16 or 17 wherein one of the first alkylating agent and the second alkylating agent is an olefinic material containing significant amounts of propylene and the other of said alkylating agents is an olefinic material containing significant amounts of butenes.

21. A method in accordance with claim 20 wherein the reaction temperature adjacent the point at which the olefinic material containing significant amounts of propylene is introduced is maintained between about 80° and about 120° F. and the reaction temperature adjacent the point at which the olefinic material containing significant amounts of butenes is introduced is maintained between about 40° and about 90° F.

22. A method in accordance with claim 1 wherein the amount of acid-soluble oil present in the separated acid phase is maintained at a predetermined amount by at least periodically determining the amount of acid-soluble oil in said separated acid phase and adjusting the amount of acid-soluble oil in said separated acid phase by removing a portion of said acid-soluble oil from said separated acid phase or adding an additional amount of acid-soluble oil to said separated acid phase.

23. A method in accordance with claim 22 wherein additional acid-soluble oil, when needed, is generated by contacting at least one olefinic hydrocarbon selected from the group consisting of $C_3$ monoolefinic hydrocarbons, $C_5$ and higher monoolefinic hydrocarbons, diolefinic hydrocarbons and mixtures containing the same with an acid-type catalyst selected from the group consisting of a portion of the separated acid phase, a portion of a separated rerun acid being returned to the reaction zone, fresh acid-type catalyst and mixtures thereof.

24. A method in accordance with claim 23 wherein the olefinic hydrocarbon utilized to generate additional acid-soluble oil is heated to a temperature above the temperature of the separated acid phase and the heated olefinic hydrocarbon is thereafter combined with said separated acid phase.

25. A method in accordance with claim 23 wherein the olefinic hydrocarbon is contacted with the acid-type catalyst to generate additional acid-soluble oil in a separate reaction zone under conditions conducive to the formation of acid-soluble oil and the generated acid-soluble oil is thereafter added to the separated acid phase.

26. Apparatus for alkylating at least one alkylatable hydrocarbon with at least two different alkylating agents at an equal number of different reaction temperatures, respectively, in the presence of an acid-type catalyst comprising:

a vertically-disposed, elongated alkylation reactor means;

first alkylating agent feed conduit means operatively connected to said reactor adjacent the bottom thereof and adapted to introduce a first alkylating agent upwardly through said reactor;

at least one additional alkylating agent feed conduit means operatively connected to said reactor at an equal number of separate points above said first alkylating agent conduit and adapted to introduce at least one additional alkylating agent upwardly through said reactor;

at least one alkylatable hydrocarbon feed conduit means operatively connected to said reactor and adapted to introduce at least one alkylatable hydrocarbon into said reactor at one of the point of introduction of said first alkylating agent, the point of introduction of said at least one additional alkylating agent or both the point of introduction of said first alkylating agent and the point of introduction of said at least one additional alkylating agent;

separator-surge means operatively connected to the upper, outlet end of said reactor and adapted to receive effluent from said reactor and to separate said effluent into a hydrocarbon product phase and a recycle catalyst phase; and recycle catalyst conduit means operatively connected to said separator-surge means and said reactor and adapted to receive the thus separated recycle catalyst phase and introduce one portion of said recycle catalyst phase into said reactor adjacent one of said point of introduction of said first alkylating agent and said point of introduction of said at least one additional alkylating agent and the remainder of said recycle catalyst phase into said reactor adjacent the other of said point of introduction of said first alkylating agent and said point of introduction of said at least one additional alkylating agent.

27. Apparatus in accordance with claim 26 wherein temperature sensing means is operatively connected to the reactor and is adapted to measure the reaction temperature at a point above one of the point of introduction of the first alkylating agent or the point of introduction of the at least one additional alkylating agent or both the point of introduction of the first alkylating agent and the point of introduction of the at least one additional alkylating agent and control means operatively connected to said temperature sensing means and to at least one of the recycle catalyst conduit means which introduces recycle catalyst phase into said reactor at a point adjacent said point of introduction of said first alkylating agent, said point of introduction of said at least one additional alkylating agent or both.

28. Apparatus in accordance with claim 27 wherein the temperature sensing means is operatively connected to the reactor at a point above the point of introduction of the first alkylating agent and the control means is operatively connected to the recycle catalyst conduit means adapted to introduce the recycle catalyst adjacent said point of introduction of said first alkylating agent.

29. Apparatus in accordance with claim 27 wherein a heat exchange means is mounted in at least one of the recycle catalyst conduit means which introduces recycle catalyst into the reactor adjacent the point of introduction of the first alkylating agent and the point of introduction of the at least one additional alkylating agent and the temperature sensing means is operatively connected to said heat exchange means to control the temperature of said heat exchange means.

30. Apparatus in accordance with claim 26 wherein a heat exchange means is mounted in at least one of the recycle catalyst conduit means which introduces recycle catalyst into the reactor adjacent the point of introduction of the first alkylating agent and the point of introduction of the at least one additional alkylating agent, a temperature sensing means is operatively connected to the reactor and is adapted to measure the reaction temperature above one of said point of introduction of the first alkylating agent and said point of introduction of the at least one additional alkylating agent and a control means is operatively connected to said temperature sensing means and said heat exchange means to adjust the temperature of said heat exchange means in accordance with the temperature sensed by said temperature sensing means.

31. Apparatus in accordance with claim 26 wherein heater means is mounted in at least one of the first catalyst recycle conduit means and the at least one additional catalyst recycle conduit means.

32. Apparatus in accordance with claim 26 wherein cooling means is mounted in at least one of the first catalyst recycle conduit means and the at least one additional recycle catalyst conduit means.

33. Apparatus in accordance with claim 26 wherein heater means is mounted in the first catalyst recycle conduit means which introduces recycle catalyst at a point adjacent the point at which the higher of the different reaction temperatures is maintained and cooling means is mounted in the recycle catalyst conduit means which introduces recycle catalyst into said reactor at a point adjacent the point at which the lower of said different reaction temperatures is maintained.

34. Apparatus in accordance with claim 26 wherein a hydrocarbon phase recycle conduit means is operatively connected to the separator-surge means and to at least one of the first alkylating agent conduit means and the at least one additional alkylating agent conduit means.

35. Apparatus in accordance with claim 26 wherein a heating means adapted to receive at least one olefinic hydrocarbon and heat said olefinic hydrocarbon to a temperature above the temperature of the recycle catalyst phase is operatively connected to the recycle catalyst conduit means to introduce said heated olefinic hydrocarbon into said recycle catalyst phase.

36. Apparatus in accordance with claim 26 wherein a second reactor means adapted to receive at least one olefinic hydrocarbon and an acid-type catalyst and react the same to produce catalyst-soluble oil is operatively connected to the recycle catalyst conduit means to introduce said produced catalyst-soluble oil into the recycle catalyst phase.

* * * * *

UNITED STATES PATENT AND TRADEMARK OFFICE
CERTIFICATE OF CORRECTION

PATENT NO. : 4,205,196

DATED : May 27, 1980

INVENTOR(S) : Donald J. Makovec et al

It is certified that error appears in the above-identified patent and that said Letters Patent are hereby corrected as shown below:

Column 12, claim 3, line 14, after "phase" and before "and" change "streams" to --- stream ---.

*Signed and Sealed this*

*Twenty-first* Day of *April 1981*

[SEAL]

Attest:

RENE D. TEGTMEYER

*Attesting Officer*    *Acting Commissioner of Patents and Trademarks*